United States Patent
Littlecreek et al.

(10) Patent No.: US 10,853,453 B1
(45) Date of Patent: Dec. 1, 2020

(54) SYSTEMS AND METHODS FOR LOGICAL DATA PROCESSING

(71) Applicant: Express Scripts Strategic Development, Inc., St. Louis, MO (US)

(72) Inventors: Laurie Littlecreek, Foristell, MO (US); Corinne Bradley-Pollack, Hillsboro, MO (US); David Hutchison, Collinsville, IL (US); Kevin Mulligan, Minneapolis, MN (US); Leah Sterman-Kabrt, West Caldwell, NJ (US); Melissa Orlando, Saint Ann, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 543 days.

(21) Appl. No.: 15/709,909

(22) Filed: Sep. 20, 2017

Related U.S. Application Data

(60) Provisional application No. 62/397,904, filed on Sep. 21, 2016.

(51) Int. Cl.
| | |
|---|---|
| *G06N 99/00* | (2019.01) |
| *G06F 19/00* | (2018.01) |
| *G06Q 10/10* | (2012.01) |
| *G06Q 10/08* | (2012.01) |
| *G06Q 50/24* | (2012.01) |

(52) U.S. Cl.
CPC ........ *G06F 19/328* (2013.01); *G06F 19/3462* (2013.01); *G06Q 10/10* (2013.01); *G06Q 10/087* (2013.01); *G06Q 50/24* (2013.01)

(58) Field of Classification Search
CPC .......... G06Q 50/24; G06Q 10/063118; G06Q 10/06; G16H 40/20; G16H 10/60; G16H 10/20; G16H 10/65; G16H 20/40; G16H 40/63; G16H 40/67; G06F 19/3456; G06F 19/328; G06F 21/6245; G06F 19/3418; G06F 19/00
See application file for complete search history.

(56) References Cited

U.S. PATENT DOCUMENTS

| | | | |
|---|---|---|---|
| 8,290,790 B1 * | 10/2012 | Jackson ................. | G06Q 10/10 705/3 |
| 8,321,243 B1 | 11/2012 | Harris, Sr. et al. | |
| 8,392,209 B1 | 3/2013 | Bertha et al. | |
| 8,781,854 B1 | 7/2014 | Harris, Sr. | |

(Continued)

*Primary Examiner* — Maroun P Kanaan
(74) *Attorney, Agent, or Firm* — Small Patent Law Group LLC

(57) ABSTRACT

A method includes receiving a data processing request at a computing system. The data processing request identifies data to be compared to sets of criteria according to a predefined sequence of the sets that is defined by a non-variant logic process. The method also includes determining whether the request is to be processed according to a variant logic process that defines a modified sequence of the criteria sets than the non-variant logic process. The method also includes dynamically altering the predefined sequence of the criteria sets to the modified sequence responsive to determining that the request is to be processed using the variant logic process, comparing the data identified by the request with the criteria sets according to the modified sequence, and processing the data according to the criteria sets of criteria in the modified sequence.

13 Claims, 7 Drawing Sheets

(56) References Cited

U.S. PATENT DOCUMENTS

| | | |
|---|---|---|
| 2009/0281823 A1 | 11/2009 | Hardaway |
| 2009/0281824 A1 | 11/2009 | Hardaway |
| 2015/0095052 A1 | 4/2015 | Weinstein |
| 2015/0205936 A1 | 7/2015 | Ford et al. |
| 2015/0261935 A1 | 9/2015 | Crockett |
| 2016/0004979 A1* | 1/2016 | Getchius ............... G06F 19/328 706/12 |
| 2016/0042147 A1 | 2/2016 | Maurer et al. |
| 2016/0092642 A1 | 3/2016 | Maurer et al. |

* cited by examiner

FIGURE 3

| Client | Network Groups | Variant |
|---|---|---|
| 42511 | 154;454;490;527 | 0 |
| 41454 | 454;490;527 | 0 |
| 41544 | 154;454;490;527 | 0 |
| 26326 | 154;454;527 | 487 |
| 40725 | 154;527 | 0 |

FIGURE 4

| Network Group | Provider A | Provider B | Provider C | Provider D | Provider E |
|---|---|---|---|---|---|
| 154 | 1 | 1 | 1 | 1 | 1 |
| 454 | 0 | 1 | 1 | 0 | 0 |
| 490 | 1 | 0 | 0 | 0 | 0 |
| 527 | 1 | 1 | 1 | 1 | 0 |

900

| Provider | NG 154 | NG 454 | NG 490 | NG 527 | Suspended | Override |
|---|---|---|---|---|---|---|
| A | 1 | 1 | 1 | 1 | 1 | 0 |
| B | 1 | 1 | 0 | 1 | 0 | 213; 133 |
| C | 1 | 0 | 0 | 1 | 0 | 133 |
| D | 1 | 0 | 0 | 0 | 0 | 0 |
| E | 1 | 0 | 0 | 0 | 0 | 0 |

| Override | Fee | Basis |
|---|---|---|
| 133 | $25 | Location |
| 213 | $35 | K |
| 245 | $5 | Other |
| 521 | $5 | Location |
| 900 | $55 | Other |
| 966 | $15 | K |

SYSTEMS AND METHODS FOR LOGICAL DATA PROCESSING

CROSS-REFERENCE TO RELATED APPLICATIONS

This application claims priority to U.S. Provisional Application No. 62/397,904, which was filed on 21 Sep. 2016, and the entire disclosure of which is incorporated herein by reference.

FIELD

The present disclosure relates generally to the technical field of data processing. In a specific example, the present disclosure may relate to the logic processing of data to improve data processing performance.

BACKGROUND

Organizations may have complex and customized data processing systems for operation management purposes. Certain systems may be easier to implement, program, and use, while other systems may be relatively more complex. Often, data processing systems that are more flexible, and provide the operators of the systems with more options (e.g., configurations, features, and the like), are more complex. Because of balancing flexibility and complexity, certain options may be limited, unavailable, more complicated to implement, or otherwise. As such, the data captured and/or used by the system may be less useful in processing due to these system limitations.

BRIEF SUMMARY

In one embodiment, a method includes receiving a data processing request at a computing system. The data processing request identifies data to be compared to various sets of criteria according to a predefined sequence of the various sets of criteria. The predefined sequence of the various sets of criteria is defined by a non-variant logic process. The method also includes determining whether the data processing request is to be processed according to a variant logic process. The variant logic process defines a modified, different sequence of the various sets of criteria than the predefined sequence defined by the non-variant logic process. The method also includes dynamically altering the predefined sequence of the various sets of criteria to the modified, different sequence of the sets of criteria responsive to determining that the data processing request is to be processed using the variant logic process, comparing the data identified by the data processing request with the sets of criteria according to the modified, different sequence that is defined by the variant logic process, and processing the data according to the sets of criteria according to the modified, different sequence that is defined by the variant logic process.

In one embodiment, a tangible and non-transitory computer-readable storage medium includes instructions that direct at least one processor to receive a data processing request at a computing system. The data processing request identifies data to be compared to various sets of criteria according to a predefined sequence of the various sets of criteria. The predefined sequence of the various sets of criteria is defined by a non-variant logic process. The instructions also direct the at least one processor to determine whether the data processing request is to be processed according to a variant logic process. The variant logic process defines a modified, different sequence of the various sets of criteria than the predefined sequence defined by the non-variant logic process. The instructions also direct the at least one processor to dynamically alter the predefined sequence of the various sets of criteria to the modified, different sequence of the sets of criteria responsive to determining that the data processing request is to be processed using the variant logic process, to compare the data identified by the data processing request with the sets of criteria in the modified, different sequence that is defined by the variant logic process, and to process the data according to the sets of criteria in the modified, different sequence that is defined by the variant logic process.

In one embodiment, a method includes receiving a data processing request at a computing system. The data processing request identifies data to be compared to various sets of criteria according to a predefined sequence of the various sets of criteria. The method also includes identifying a suspended set of criteria from among the various sets of criteria in the predefined sequence. The suspended set of criteria includes a set of criteria associated with a pharmaceutical provider having a suspended license. The method also includes dynamically altering the predefined sequence of the various sets of criteria to a modified sequence by eliminating the suspended set of criteria from the predefined sequence, comparing the data identified by the data processing request with the sets of criteria in the modified sequence subsequent to elimination of the suspended set of criteria, and processing the data according to the sets of criteria in the modified sequence.

BRIEF DESCRIPTION OF THE DRAWINGS

The present disclosure will become more fully understood from the detailed description and the accompanying drawings.

FIG. 3 illustrates one example of a data structure representative of variant data shown in FIG. 2 according to one example embodiment;

FIG. 4 illustrates one example of a data structure representative of network data shown in FIG. 2 according to one example embodiment;

FIG. 6 illustrates one example of a data structure representative of provider data shown in FIG. 2 according to one example embodiment;

FIG. 7 illustrates one example of a data structure representative of override data shown in FIG. 2 according to one example embodiment;

DETAILED DESCRIPTION

Figure 1:
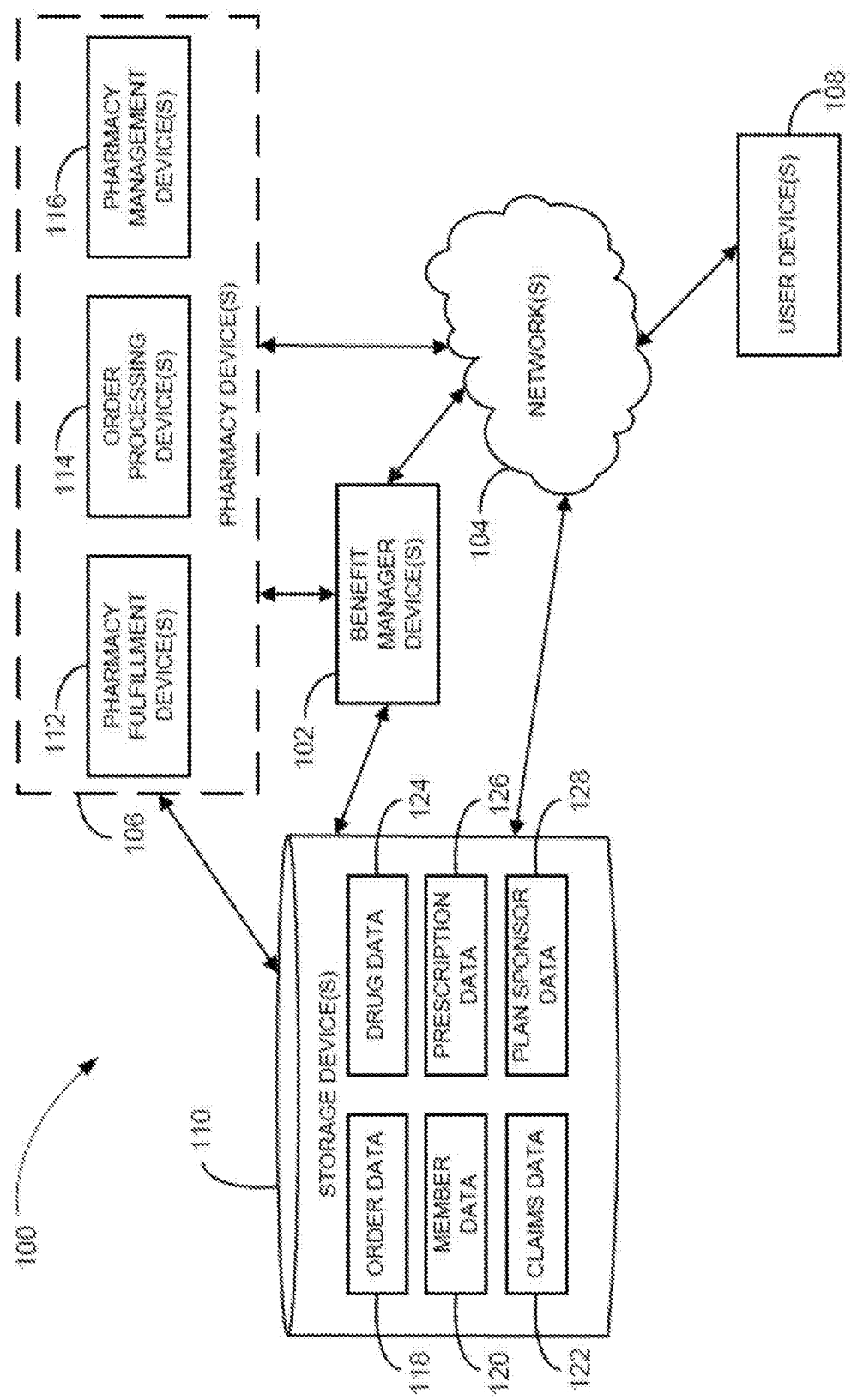
FIG. 1 is a diagram of an example implementation of a system for a pharmacy, according to an example embodiment.

Example systems and methods for logical data processing, for example, by a pharmacy benefits manager (PBM), are described. In the following description, for purposes of explanation, numerous specific details are set forth in order to provide a thorough understanding of example embodiments. It will be evident, however, to one of ordinary skill in the art that these embodiments may be practiced without these specific details.

A large amount of data may be used to determine which pharmacies can process and fill the prescriptions and prescription orders, and how the prescriptions and prescription orders are processed and filled by the pharmacies. This data can be extensive and complex due to the vast amount of pharmacies and other providers, as well as the arrangements for which pharmacies and other providers are permitted to process and fill prescriptions and prescription orders for a large number of different purchasers having a large amount of different insurance plans.

Service level agreements (SLA) between pharmacy benefit managers and its clients may require that the benefit managers process a claim for pharmacy benefits under one or more than one insurance plans within a short time period. In some embodiments, that time period may be subject to a contractual agreement between the pharmacy benefit manager and the insurance plan. In order to quickly process claims, the pharmacy benefit manager may create groups of pharmaceutical providers (e.g., pharmacies) that are approved for the claims.

These groups (also referred to as networks or pharmacy networks) can be contractually associated with different insurance plans. Claims may be processed quickly by comparing the provider submitting the claim with the approved providers with the provider network.

But, various restrictions in different areas of the country, in different contracts with insurance plans, or the like, may necessitate changes or variations to the provider networks and/or the providers approved for the claims. For example, one geographic area may enact a law or regulation that changes allowable medications and/or allowable amounts to be collected from consumers for certain medications. As another example, one or more than one pharmaceutical provider may be temporarily suspended from processing claims due to issues with certification of the pharmaceutical providers.

In order to accommodate these various restrictions, the details of the provider networks and/or the providers in the provider networks may be modified in the software applications that process the claims. These modifications can include individualized modifications for the locations and/or providers associated with the restrictions. However, making these modifications can require extensive, costly, and time-consuming labor via manual data entry.

In currently known systems, a claim for pharmacy benefits is submitted to a pharmacy benefit manager from a pharmaceutical provider. The pharmacy benefit manager receives the claim and processes the claim by, among other things, determining if the pharmaceutical provider is included in one or more the one network of providers attached to a client (for example, an insurance plan). The client may have several different networks, such as one network that includes a fewer number of approved pharmaceutical providers but also includes reduced prices for the client, another network that includes a greater number of approved pharmaceutical providers but also includes increased prices for the client, another network to provide specialized medical products, and so on.

The pharmacy benefit manager may apply a processing logic to determine whether a claim for a pharmaceutical benefit is to be denied. This processing logic can be interfered with or negated by client requests for solutions that are inconsistent or incompatible with each other. For example, a client may request benefits for insurance plan members of the client that result in contradictions or incorrect processing of claims submitted for the normal, customary logic applied in processing the claims.

The pharmacy benefit manager may manage claims for many different clients (e.g., insurance companies). In order to efficiently process claims in short processing time periods, the pharmacy benefit manager may offer some or all of the same groups of provider networks to the different clients. This can ease the processing time for claims relative to each client having a separate, individualized network of approved providers.

Variations in these provider networks may apply for one or more than one of the clients. For example, a client may request inconsistent or incompatible benefits that cause some claims to be incorrectly denied by the processing logic used by the pharmacy benefit manager.

In some embodiments, the systems and methods process pharmaceutical data, such as benefit claims, by varying from the processing logic usually used to process the claims responsive to one or more variables appearing in or associated with a claim. For example, when the pharmacy benefit manager is presented with multiple variables in a claim (e.g., different medications, different amounts of medications, telecommunication data fields or segments submitted on an electronic pharmacy claim, etc.), a variant logic may be applied based on one or more of these variables to avoid negating or violating the intent or goal of the variables.

Without use of the present methods and systems, extensive writing and/or rewriting of data on a client-by-client basis may be performed in order to account for each individual client's requested benefits to members of the client's plan. The systems and methods described herein allow for these variations to be quickly accounted for, without extensive writing or rewriting of data. These variations are accounted for without significantly delaying the processing time for benefits submitted by various providers.

FIG. 1 is a block diagram of an example implementation of a system 100 for a pharmacy, according to an example embodiment. The system 100 is an example environment in which the methods and systems for logical data processing may be implemented. However, the methods and systems may be implemented in data processing environments that are not associated with pharmacy technology. For example, the methods and systems may be implemented in other systems where there are varying networks of benefits such as insurance benefit networks, dental benefit networks, and the like.

While the system 100 is generally described as being deployed in a high-volume pharmacy or a fulfillment center (e.g., a mail order pharmacy, a direct delivery pharmacy, etc., and the like), the system 100 and/or components thereof may otherwise be deployed (e.g., in a lower volume pharmacy, etc.). A high-volume pharmacy may be a pharmacy that is capable of filling prescriptions automatically, mechanically, manually, or a combination thereof. The system 100 may include a benefit manager device 102, a pharmacy device 106, and a user device 108 in communicating with each other directly and/or over a network 104.

The system may also include a storage device 110.

The benefit manager device 102 is a device operated by an entity that is at least partially responsible for creation and/or management of the pharmacy or drug benefit. While such entity operating the benefit manager device 102 is typically a pharmacy benefit manager, other entities may operate the benefit manager device 102 on behalf of themselves (i.e., the pharmacy benefit managers) or other entities. For example, the benefit manager device 102 may be operated by a health plan, a retail pharmacy chain, a drug wholesaler, a data analytics, or other type of software-related company, etc., or the like. In some embodiments, a pharmacy benefit manager that provides the pharmacy benefit may also provide one or more than one additional benefits including a medical or health benefit, a dental benefit, a vision benefit, a wellness benefit, a radiology benefit, a pet care benefit, an insurance benefit, a long-term care benefit, a nursing home benefit, etc., and the like. The pharmacy benefit manager may, in addition to its pharmacy benefit manager operations, operate one or more than one pharmacies. The pharmacies may be retail pharmacies, mail order pharmacies, etc.

Some of the operations of the pharmacy benefit manager that operates the benefit manager device 102 may include the following activities and processes. A member (or a person on behalf of the member) of a pharmacy benefit plan may obtain a prescription drug at a retail pharmacy location (e.g., a location of a physical store, etc.) from a pharmacist or a pharmacist technician.

The member may also obtain the prescription drug through mail order drug delivery from a mail order pharmacy location, which may be the pharmacy system 100. In some embodiments, the member may obtain the prescription drug directly or indirectly using a machine, such as a kiosk, vending unit, mobile electronic device, or a different type of mechanical, electrical, electronic communication device and/or computing device. Such a machine may be filled with the prescription drug in prescription packaging, which may include multiple prescription components, by the pharmacy system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, etc., or the like. In some instances, an employer of the member may directly or indirectly fund or reimburse the member for the copayments.

The amount of the copayment required by the member may vary with different pharmacy benefit plans having different plan sponsors or clients and/or for different prescription drugs. The member's copayment may be a flat copayment (e.g., $10, etc.), co-insurance (e.g., 10%, etc.), and/or a deductible (e.g., for first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels used for the prescription drug to be received. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the pharmacy benefit manager for the prescription drug. After receiving the claim, the pharmacy benefit manager, e.g., the benefit manager device, may perform certain adjudication operations including verifying eligibility for the member, identifying/reviewing an applicable formulary for the member to determine any appropriate copayment, coinsurance, and deductible for the prescription drug, and performing a drug utilization review (DUR) on the member. Further, the pharmacy benefit manager may provide a response to the pharmacy, e.g., the pharmacy system 100, following performance of at least some of the aforementioned operations.

As part of the adjudication, a plan sponsor (or the pharmacy benefit manager on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However, in some instances, these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on types of pharmacy network in which the pharmacy is included. In some embodiments, the amount may also be determined based on other factors. For example, if the member pays the pharmacy for the prescription drug without using the prescription or drug benefit provided by the pharmacy benefit manager, the amount of money paid by the member may be higher than when the member uses the prescription or drug benefit. In some embodiments, the amount of money received by the pharmacy for dispensing the prescription drug and for the prescription drug itself may be higher than when the member uses the prescription or drug benefit. Some or all the foregoing operations may be performed by executing instructions stored in the benefit manager device 102 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a Wi-Fi network, or an IEEE 802.11 standards network, as well as various combinations thereof. The network 104 may include optical network. The network 104 may be a local area network or a global communication network, such as the Internet. In some embodiments, the network 104 may include a network dedicated to prescription orders, e.g., a prescribing network such as the electronic prescribing network operated by Surescripts of Arlington, Va.

Moreover, although the system shows a single network 104, multiple networks can be used. The multiple networks may communicate in series with each other to link the devices 102, 106-110 or in parallel to link the devices 102, 106-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy device 106 may be utilized by the pharmacy to submit the claim to the pharmacy benefit manager for adjudication.

Additionally, in some embodiments, the pharmacy device 106 may enable information exchange between the pharmacy and the pharmacy benefit manager, for example, to allow the sharing of member information such as drug history, and the like, that may allow the pharmacy to better service a member (e.g., by providing more informed therapy consultation and drug interaction information, etc.). In some embodiments, the benefit manager device 102 may track prescription drug fulfillment and/or other information for patients that are not members or have not identified themselves as members, at the time (or in conjunction with the time) in which they seek to have a prescription filled at a pharmacy.

The pharmacy device 106 may include an order processing device 114, a pharmacy management device 116, and a pharmacy fulfillment device 112 in communication with each other directly and/or over the network 104.

The order processing device 114 may receive information regarding filling prescriptions and may direct an order component to one or more devices of the pharmacy fulfillment device 112 at a pharmacy. The fulfillment device 112 may fulfill, dispense, aggregate, and/or pack the order components of the prescription drugs in accordance with one or more prescription orders directed by the order processing device 114. The order processing device 114 may be deployed in the system 100, or may otherwise be used.

In general, the order processing device 114 is a device located within or otherwise associated with the pharmacy to enable fulfillment of a prescription and dispensing prescription drugs by the fulfillment device 112. In some embodiments, the order processing device 114 may be an external device separate from the pharmacy and communicate with other devices located within the pharmacy.

For example, the external order processing device 114 may communicate with an internal order processing device 114 and/or other devices located within the system 100. In some embodiments, the external order processing device 114 may have limited functionality (e.g., as operated by a patient requesting fulfillment of a prescription drug), while the internal pharmacy order processing device 114 may have greater functionality (e.g., as operated by a pharmacist).

The order processing device 114 may track the prescription order as it is fulfilled by the pharmacy fulfillment device 112. The prescription order may include one or more than one prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a patient or a patient family. The order processing device 114 may also track and/or schedule literature or paperwork associated with each prescription order or multiple prescription orders that are being shipped together.

Generally, a prescription order is generated for a pharmacy. The prescription order may include more than one prescription drug for fulfillment. Each prescription drug in a prescription order is an order component of the prescription order. Generally, the order components are pill bottles, liquid bottles, blister packs, unit-of-use packs, injectable package, spray bottles, tubes, ampoules, drop counters, insulated boxes, child-resistant containers, or other packaging having a quantity of a prescription drug contained therein.

In some embodiments, the order processing device 114 may operate in combination with the pharmacy management device 116.

The order processing device 114 may include circuitry, a processor, a memory to store data and instructions, and communication functionality. The order processing device 114 is dedicated to performing processes, methods and/or instructions described herein. Other types of electronic devices specifically configured to implement with the processes, methods and/or instructions described herein may also be used.

In some embodiments, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (e.g., by utilizing a local storage, etc.) and/or through the network 104 (e.g., by utilizing a cloud configuration or software as a service, etc.) with the storage 110.

The user device 108 is used by a device operator. The device operator may be a user (e.g., an employee, a contractor, a benefit member, etc.) associated with a software development project. Other device operators may also operate the user device 108.

The user device 108 may be a stand-alone device that solely provides at least some of the functionality of the methods and systems, or may be a multi-use device that has functionality outside of analysis of the methods and systems. Examples of the user device 108 include a set-top box (STB), a receiver card, a mobile telephone, a personal digital assistant (PDA), a display device, a portable gaming unit, and a computing system, etc. Other devices, however, may also be used. In some embodiments, the computing system may include a mobile computing device. For example, the user device 108 may include a mobile electronic device, such an iPhone or iPad by Apple, Inc., mobile electronic devices powered by Android by Google, Inc., and a Blackberry by BlackBerry Limited. The user device 108 may also include other computing devices, such as desktop computing devices, notebook computing devices, netbook computing devices, gaming devices, and the like. Other types of electronic devices may also be used.

The storage device 110 may include: a non-transitory storage (e.g., memory, hard disk, CD-ROM, etc.) in communication with the benefit manager device 102, the pharmacy device 106, and/or the user device 108 directly and/or over the network 104. The non-transitory storage may store pharmaceutical data such as order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (e.g., drug name and strength, etc.) and quantity of the prescription drug, etc. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 118 may be used by a fulfillment center to fulfill a pharmacy order.

In some embodiments, the order data 118 includes verification information associated with fulfillment of the prescription in the pharmacy. For example, the order data 118 may include videos and/or images taken of: (i) the prescription drug prior to dispensing, during dispensing, and/or after dispensing, (ii) the prescription container (e.g., a prescription bottle and sealing lid, prescription packaging and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets, bins, trays, carts, and the like used to transport prescriptions within the pharmacy may also be stored as order data 118.

The member data 120 includes information regarding the members associated with the pharmacy benefit manager. The information stored as member data 120 may include personal information, personal health information, protected health information, and the like. Examples of the member data 120 include name, address, telephone number, e-mail address, prescription drug history, etc., and the like. The member data 120 may include a plan sponsor identifier that identifies the plan sponsor associated with the member and/or a member identifier that identifies the member to the plan sponsor. The member data 120 may include a member identifier that identifies the plan sponsor associated with the patient and/or a patient identifier that identifies the patient to the plan sponsor. The member data 120 may also include, by way of example, dispensation preferences such as type of label, type of cap, message preferences, language preferences, or the like.

The member data 120 may be accessed by various devices in the pharmacy (e.g., the fulfillment center, etc.) to obtain information utilized for fulfillment and shipping of prescription orders. In some embodiments, an external order processing device 114 operated by or on behalf of a member may have access to at least a portion of the member data 120 for review, verification, etc., or other purposes.

In some embodiments, the member data 120 may include information for persons who are patients of the pharmacy but are not members in the pharmacy benefit plan being provided by the pharmacy benefit manager. For example, these patients may obtain drug directly from the pharmacy, through a private label service offered by the pharmacy, the fulfillment center, or otherwise. In general, the use of the terms member (e.g., of a prescription drug plan) and patient (e.g., of a pharmacy) may be used interchangeably herein.

The claims data 122 includes information regarding pharmacy claims adjudicated by the pharmacy benefit manager under a drug benefit program provided by the pharmacy benefit manager for one, or more than one, plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copay/coinsurance amount, rebate information, and/or member eligibility, and the like. Additional information may be included.

In some embodiments, other types of claims beyond prescription drug claims may be stored in the claims data 122. For example, medical claims, dental claims, wellness claims, or other type of health care-related claims for members may be stored as a portion of the claims data 122.

In some embodiments, the claims data 122 includes claims that identify the members with whom the claims are associated. In some embodiments, the claims data 122 includes claims that have been de-identified (e.g., associated with a unique identifier but not with a particular, identifiable member), aggregated, or otherwise processed.

The drug data 124 may include drug name (e.g., technical name and/or common name, etc.), other names by which the drug is known by, active ingredients, an image of the drug (e.g., in pill form, etc.), and the like. The drug data 124 may include information associated with a single medication or multiple medications.

The prescription data 126 may include information regarding prescriptions that may be issued by prescribers on behalf of patients, who may be members of the pharmacy benefit plan, for example to be filled by a pharmacy. Examples of the prescription data 126 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 118 may be linked to associated member data 120, claims data 122, drug data 124, and/or prescription data 126.

The plan sponsor data 128 includes information regarding the plan sponsors of the pharmacy benefit manager. Examples of the plan sponsor data 128 include company name, company address, contact name, contact telephone number, contact e-mail address, etc., and the like.

Figure 2:
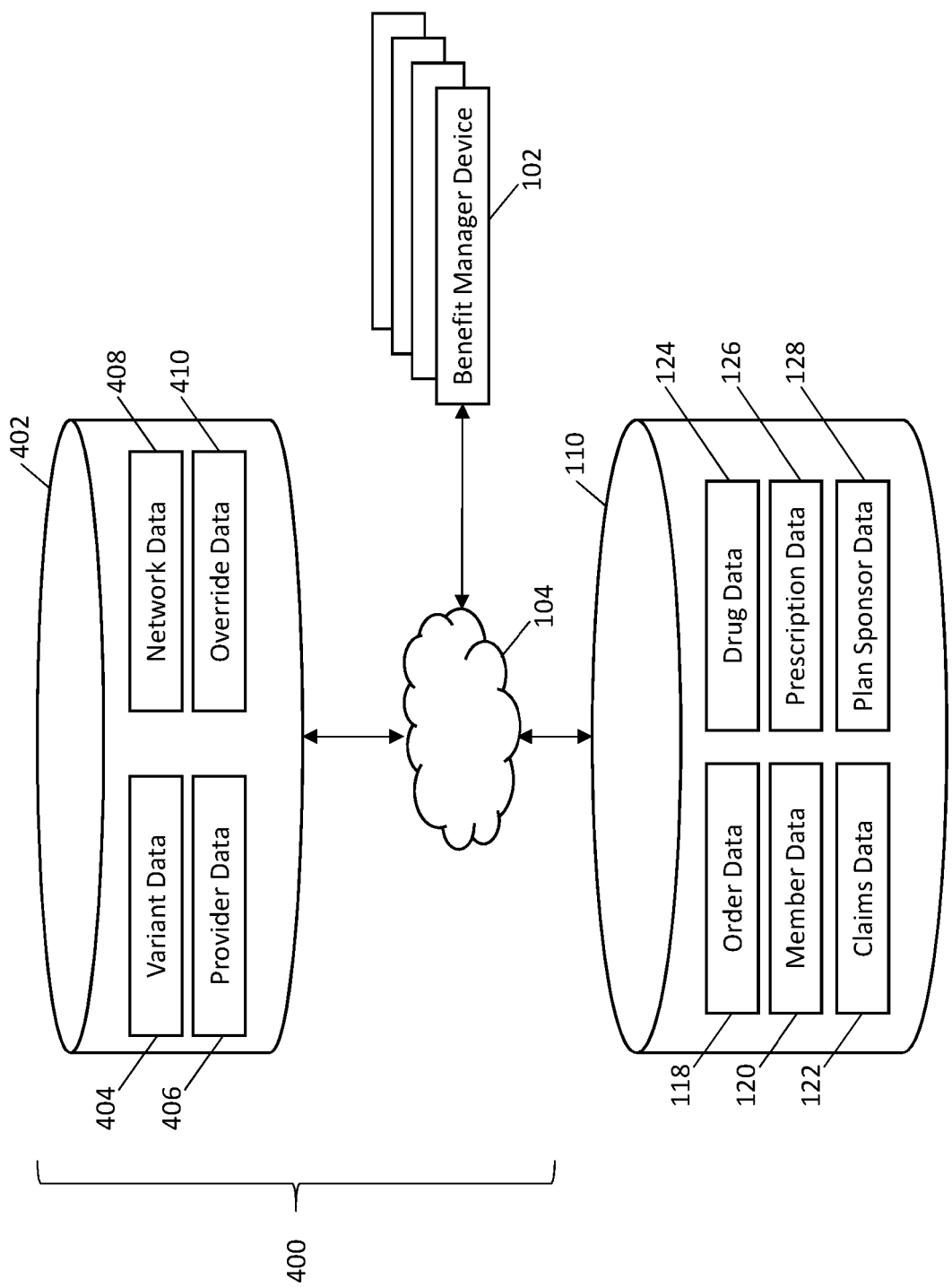
FIG. 2 is a block diagram of an example implementation of a system for processing pharmaceutical data, according to an example embodiment.

FIG. 2 is a block diagram of an example implementation of a system 400 for processing pharmaceutical data, according to an example embodiment. While the system 400 is generally described as being deployed for use in processing claims data for pharmaceutical benefits, the system 400 and/or components thereof may otherwise be deployed.

The system 400 includes a single or multiple benefit manager devices 102 (see FIG. 1). The benefit manager device 102 represent hardware circuitry that includes and/or is connected with one or more than one processors (e.g., microprocessors, field programmable gate arrays, integrated circuits, or the like) that operate to perform various operations to control the processing of pharmaceutical benefits, including accounting for variations in the provider networks attached to a client (e.g., contractually agreed to by the client), accounting suspensions of providers from processing claims data for the client, and/or accounting for changes in the contractually agreed upon amounts charged for medications.

The benefit manager device 102 communicates with the storage device 110 and/or one or more additional storage devices 402 (e.g., the network 104) to access information used to quickly determine what processing logic is to be used for processing or otherwise analyzing data processing requests. In one embodiment, the data processing requests are received by the system 400 and identify one or more medications to be administered by a pharmacy. The data processing requests can represent or otherwise include claims for pharmaceutical benefits submitted by members of plans (e.g., insurance plans) provided by various clients of the pharmacy benefit manager. The requests are processed by the computing system 400 to quickly determine whether to approve or deny the claim for pharmaceutical plan benefits, to quickly determine what override fees to charge for medications of one or more than one provider, and/or to quickly determine which providers are currently suspended (and thereby unable to fill pharmacy orders). While the storage devices 110, 402 are shown as separate devices in FIG. 2, the storage devices 110, 402 may be combined into a single storage device, may be split among more than two storage devices 110, 402, or otherwise. In some embodiments, the storage devices 110, 402 may be deployed in memory, disk storage, or otherwise of a computer system.

Variant data 404 may be stored in the additional storage device 402 and represent data structures that indicate which processing logic is to be used for examining claims for pharmaceutical benefits for different clients. The data structures within the variant data 404 also include data indicative of whether or not one or more than one variations, or variant networks, are attached to one or more than one of the clients. In general, a variant network includes a group of approved providers that is added to a group of provider networks of a client to ensure that the pharmaceutical benefits sought to be provided by the client to members of the client's plan(s) are provided to the members. As such, the variant data 404 generally defines data that is used by a variant processing logic to modify a predefined data processing order for claims for pharmaceutical benefits. In some embodiments, the use of the variant data 404 in combination with the processing logic improves the performance of a computer processor with processing claims data 122.

For example, data sets may represent different networks of approved providers. Other data may indicate which group of networks of approved providers is associated with or available to members of an insurance plan. In some, but not all, instances, if a benefit requested by a client results in an additional network being added to the data set of networks of approved providers, this additional network may be added to the data set as a variant network of the insurance plan. The variant data 404 indicates whether the processing logic used to process claims submitted by members of certain clients is to have a variation, or variant logic, applied that deviates from the processing logic used to process claims of members of other clients. Otherwise, the normal or non-variant logic process is used.

Provider data 406 may be stored in the additional storage device 402 and represent data structures that associate different provider networks with different providers. The data included in these data structures can be examined in order to determine which providers are approved for different provider networks.

Network data 408 may be stored in the additional storage device 402 and represent data structures that associate different data elements specific to different providers and the ability of the providers to successfully process a claim through the benefit manager device 102, including specifics on whether the provider is suspended from claims processing. A fee override or override rule may apply to one or more providers, and can include a change in the financial cost that a provider charges for one or more than one medications that differ from the financial cost otherwise associated with the provide network in which the provider is included.

For example, the contract between the pharmacy benefit manager and an insurance company may dictate prices to be charged for various medications from the providers approved in a network. These prices may be overridden by changes in legislation, changes in the contract between the pharmacy benefit manager and insurance company, or other reasons. The network data 408 includes data indicative of whether or not a fee override applies, and which fee overrides apply to pharmaceutical benefit claims.

Override data 410 may be stored in the additional storage device 402 and represent data structures that associate different indications of fee overrides with the bases, causes, or reasons for the fee overrides and, in some embodiments, with the amount of the fee override.

The normal processing logic (e.g., non-variant logic process) used by the benefit manager device 102 to determine whether a claim for pharmaceutical benefits is to be denied may involve comparing details of the claim to different sets of requirements or criteria. These requirements or criteria may be obtained from or based on the various provider networks associated with a client that provides insurance plans to its members. The client may select some benefits, however, that can contradict each other. For example, the client may request a first benefit that at least partially pays for medications for a first time period (e.g., thirty days) and a second benefit that at least partially pays for medications for a different, second time period (e.g., ninety days). The normal processing logic may result in a claim being denied if the details of the claim do not meet the requirements or criteria of the first benefit, even though the details of the claim may meet the requirements or criteria of the second benefit.

In order to avoid this incorrect denial of a claim, the benefit manager device 102 may examine the data structures described herein to determine whether the client is associated with variant logic (e.g., a variant network) and, if so, to change the logic used to process the claim to avoid the claim being denied. For example, the variant logic used for such a client may ensure that the claim meeting the requirements or criteria of the second benefit (but not meeting the requirements or criteria of the first benefit) is not denied on this basis alone.

For example, a data processing request may include data identifying one or more medications to be administered or otherwise served by a pharmacy. This data can include claims data 122. The benefit manager device 102 can examine this data to determine whether a variant logic process is to be used to examine the claim for pharmaceutical benefits. In one embodiment, if the data identifies one or more medications that match (e.g., are the same as) a pre-defined medication associated with the variant logic process), then the benefit manager device 102 determines that the variant logic process is to be used. But, if the data does not identify any medication that matches the predefined medication associated with the variant logic process, then the benefit manager device 102 determines that the non-variant logic process is to be used.

As another example, a data processing request may include data identifying an amount of one or more medications to be administered or otherwise served by a pharmacy. The benefit manager device 102 can examine this data to determine whether a variant logic process is to be used to examine the claim for pharmaceutical benefits. In one embodiment, if the data identifies an amount of one or more medications that exceeds a designated or pre-defined limit associated with the non-variant logic process, then the benefit manager device 102 determines that the variant logic process is to be used. But, if the data does not identify any amount of medication that exceeds the limit, then the benefit manager device 102 determines that the non-variant logic process is to be used.

If the variant logic process is not to be used, then a non-variant logic process is used to examine the claim. The non-variant logic process identifies or defines a sequence or order of various (e.g., different) sets of criteria. Each set of criteria can be associated with a different provider of pharmaceutical benefits. The sets of criteria can define requirements of various pharmaceutical networks for approving or denying claims for pharmaceutical benefits.

The data or information in a data processing request can be compared by the benefit manager device 102 with the criteria in a first criteria set (which can be associated with a first provider of pharmaceutical benefits or a first pharmacy). If the claim is approved (e.g., by meeting or otherwise satisfying the rules of the first criteria set, which can define which medications can be administered, how much medication can be administered at one time, etc.), then processing of the claim may end. If the claim is not approved (e.g., the data violates one or more of the criteria in the first set), then the non-variant logic process can continue by examining the claim data against the criteria in a different, second set of criteria (e.g., associated with a different, second provider). This process of comparing the data to the criteria in each set can continue in the sequence of the sets of criteria defined by the non-variant logic process until the claim is approved or until it is determined that the claim does not meet or satisfy the criteria of any set (where the claim would be denied).

But, if the variant logic process is to be used, then a different, variant logic process is used to examine the claim. The variant logic process identifies or defines a difference sequence or order of various (e.g., different) sets of criteria. For example, implementation of the non-variant logic process may compare the claim against the criteria in a first set of criteria, then against the criteria in a second set of criteria, and finally against the criteria in a third set of criteria. Implementation of the variant logic process, however, can change this sequence. For example, implementation of the variant logic process may compare the claim against the criteria in the first set of criteria, then against the criteria in a fourth set of criteria, then against the criteria in a second set of criteria, and finally against the criteria in a third set of criteria.

FIG. 3 illustrates an example of a data structure 600 that is representative of the variant data 404 shown in FIG. 2 according to an example embodiment. While the data structure 600 is represented in FIG. 3 graphically, it should be appreciated that the data structure 600 may be implemented in a computer system (e.g., in a file allocation table and data associated therewith) in memory, drive storage, and/or cloud storage, or otherwise implemented.

The data structure 600 includes several records 602 each associated with a different client. The records 602 each include several cells 604, 606, 608 including data representative of different information used to process submitted claims. The client cells 604 include client identifier data that uniquely identifies different clients. The different clients represented by each client cell 604 can be entities having contractual arrangements with a pharmacy benefit manager for processing claims for pharmaceutical benefits. For example, the client identifier 42511 can represent a first insurance company, the client identifier 41454 can represent a different, second insurance company, and so on.

The network groups cells 606 include network identifier data. The network identifier data includes unique identifiers for different networks of approved providers. Depending on the contractual arrangement between the client and the pharmacy benefit manager, different clients may be associated with different provider networks. Each unique identifier of a provider network represents a different network of approved providers. In the illustrated example, the client having the identifier 42511 has agreed to pay pharmaceutical benefits for several networks of approved providers, including the providers in the provider networks having the identifiers 154, 454, 490, and 527. The client having the identifier 41454 has agreed to pay pharmaceutical benefits for some, but not all, of the providers in the same networks having the identifiers 454, 490, and 527.

The cells 608 include variant identifier data. The variant identifier data indicates whether a different, or variant, logic is to be applied during processing of submitted claims associated with the corresponding client. For example, the client having the identifier 26326 has agreed with the pharmacy benefit manager to pay pharmaceutical benefits to the providers included in the networks having identifiers 154, 454, and 527. The data in the cell 608 for the record 602 associated with this client indicates that a variant logic is to be used for this client by identifying a provider network that is added to the group of provider networks for which the client will pay pharmaceutical benefits. The value of zero or the absence of a network identifier in the cells 608 may be used to indicate that the normal or usual processing logic (e.g., not variant logic) is to be used for the corresponding client. In some embodiments, another value may be used in the cells 608 to indicate that variant logic is not to be used for the corresponding client.

The data structure 600 can allow for the pharmacy benefit manager to easily and quickly determine how to examine a submitted claim for pharmacy benefits when a variant logic applies to a client. During examination of a submitted claim, the benefit manager device 102 may query the data structure 600 for the record 602 corresponding with the client through which the claim is submitted via a provider. If the cell 608 for a client indicates that variant logic applies to the client, then the benefit manager device 102 can examine the claim by using a variant logic. This can involve determining whether the claim can be approved for payment via one or more variant networks of providers without having to change the process used to examine claims submitted for other clients that are not associated with variant logic.

FIG. 4 illustrates one example of a data structure 700 that is representative of the network data 408 shown in FIG. 2 according to an example embodiment. While the data structure 600 is represented in FIG. 4 graphically, it should be appreciated that the data structure 700 may be implemented in a computer system (e.g., in a file allocation table and data associated therewith) in memory, drive storage, and/or cloud storage, or otherwise implemented.

The data structure 700 includes several records 702 each associated with a different network of approved providers. The records 702 each include several cells 704-714 including data representative of whether various providers are included as an approved provider in the corresponding network. The data structure 700 may be used by the benefit manager device 102 to quickly determine which providers are included in a network of approved providers.

The network group cells 704 include the network identifiers described above (e.g., in connection with the cells 606 of the data structure 600). Each of the different cells 706-714 is associated with a different pharmaceutical provider. For example, the cell 706 in each record 702 may be associated with a first pharmacy ("Provider A"), the cell 708 in each record 702 may be associated with a second pharmacy ("Provider B"), and so on.

The value of the data in the cells 706-714 indicates whether the corresponding provider is included in a provider network. A value of one (or another value) in one or more than one of the cells 706-714 can indicate that the corresponding provider is included in a provider network, while another value (e.g., zero or another value) can indicate that the corresponding provider is not included in the provider network. While the data structure is reflected as having binary data, other non-binary data may be stored in the data structure 700.

In the illustrated example, the network associated with the identifier 154 includes all of Providers A, B, C, D, and E, the network associated with the identifier 454 includes the Providers B and C, the network associated with the identifier 490 includes only Provider A, and the network associated with the identifier 527 includes Providers A, B, C, and D.

Figure 5:
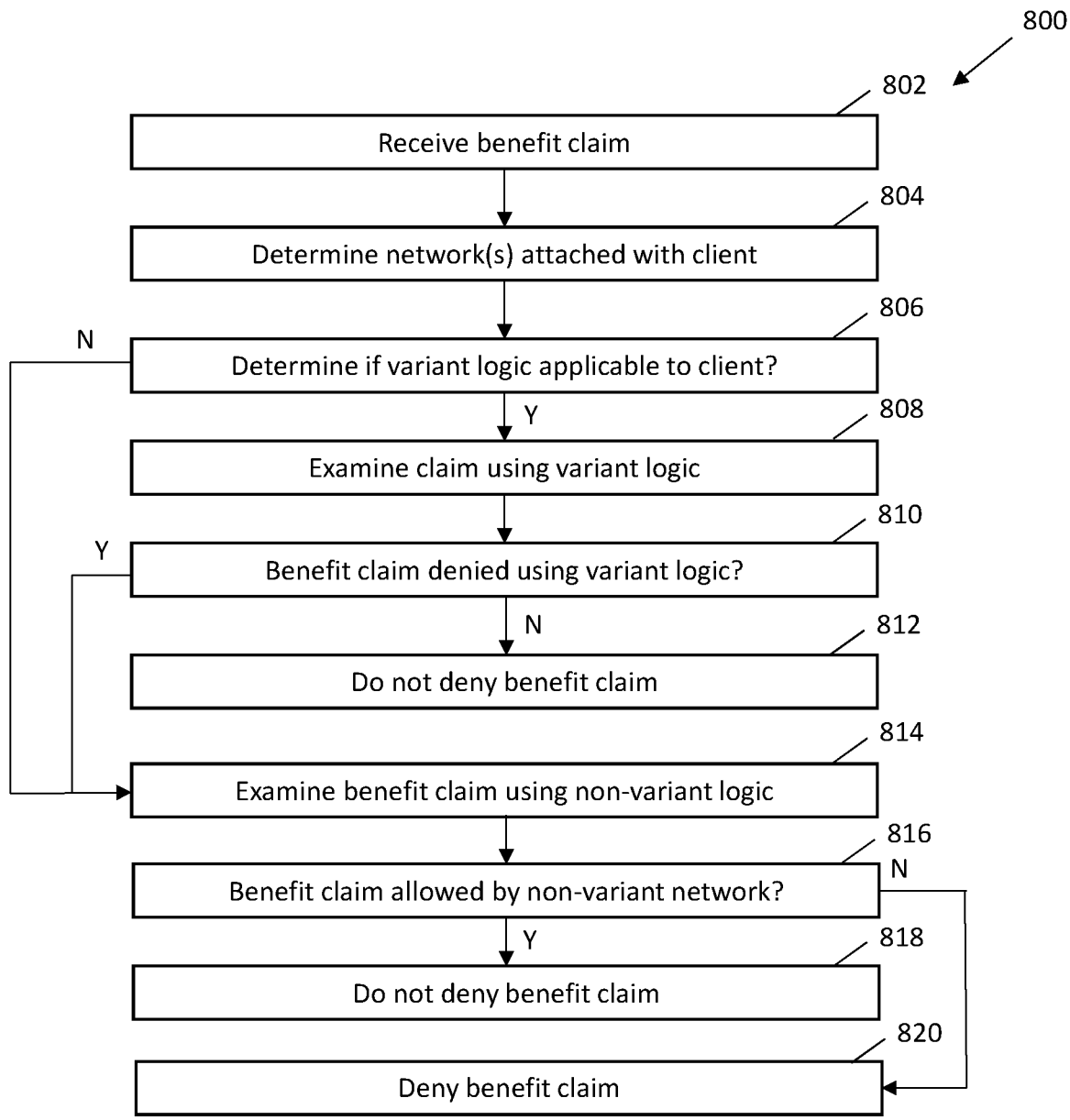
FIG. 5 is an example process flow illustrating a method for configuring data storage devices for use in processing pharmacy data according to an example embodiment.

FIG. 5 is an example process flow illustrating a method 800 for configuring data storage devices for use in processing pharmacy data according to an example embodiment. The method 800 may be used to create and/or use the data structures 600, 700 stored in one or more than one of the storage devices 110, 402 in order to process claims for pharmaceutical benefits.

At block 802, a benefit claim is received. The claim for a pharmaceutical benefit may be received via one or more than one input devices of the benefit manager device 102. In some embodiments, the benefit claim is received through an application programming information (API). In some embodiments, the benefit claim is accessed from the claims data 122. The benefit claim may identify the provider submitting the claim, the member of the insurance plan attempting to purchase medication or other pharmaceutical benefits from the provider, the client of the pharmacy benefit manager providing a pharmaceutical benefit (for example, an insurance company), and/or other information (e.g., usable to process the benefit claim).

At block 804, the provider network or provider networks attached with the client are determined. The client may be attached to one or more than one networks of approved providers by agreeing with the pharmacy benefit manager to pay at least some claims for pharmaceutical benefits submitted by the approved providers. The provider networks that are attached with the client can be determined by the benefit manager device 102 examining the data structure 600. In some embodiments, the benefit manager device 102 identifies the client in the cells 604 of the data structure 600 and obtains the identifiers of the provider networks attached to that client in the cell 606 of the same record 602 of the client in the data structure 600.

At decision point 806, a determination is made as to whether variant logic is to be used for the claim. As described above, a client may wish to add one or more than one pharmaceutical benefits to members of a plan provided by the client. These benefits may contradict each other in such a way that a valid claim for a benefit may be incorrectly denied by the normal claim processing logic. In order to prevent the benefits from being incorrectly denied, one or more than one provider network may be added to the group of provider networks associated with the client. These additional networks can be referred to as variant networks. The benefit manager device 102 can determine whether a variant logic is to be used to process claims for benefits provided by a client by examining the data structure 600. For example, the benefit manager device 102 can examine the cell 608 for the record 602 corresponding with the client. If the cell 608 includes the identifier indicative of variant logic (e.g., by identifying one or more than one variant provider networks, then the benefit manager device 102 can determine that a variant logic is to be used to process the claim.

If a determination is made that a variant logic is to be used, then flow of the method 800 may proceed to block 808. However, if a determination is made at decision point 806 that the variant logic is not to be used and the normal logic is to be used to process the claim, the flow of the method 800 may proceed to decision point 814.

At block 808, the claim is processed using the variant logic, which can be of one or more than one variant logics used. The variant logic may result in the claim being examined under a different set of rules or criteria than would otherwise be used to examine the claim, such as by comparing details of the claim to the requirements or criteria of one or more than one variant network. Not only does the claim processing differ based on which variant logic is used, but the rules used for processing the claim and that are embedded within the different variant logics are interrogated for processing the claim.

The variant logic may be applied by identifying networks that are attached to the client based on the identifiers included in the cell 608. In the example illustrated in the data structure 600 shown in FIG. 3, the client having the identifier 26326 in the cell 604 is attached with a network having an identifier of 487.

At block 810, a determination is made as to whether the claim is denied using the variant logic. For example, the data representative of the claim may be compared to the requirements or criteria of a variant network associated with the client. With respect to the example represented by the data structure 600 shown in FIG. 3, the benefit manager device 102 can examine the rules or criteria associated with the variant network having identifier 487 to determine whether the submitted claim meets or complies with these rules or criteria. If the claim does not violate the rules or criteria of the variant logic (e.g., the variant network), flow of the method 800 may proceed to block 812. At block 812, the benefit claim may not be denied by satisfying the rules or requirements of a variant network, and further examination or processing of the claim may proceed to determine whether the claim is approved for payment. In some embodiments, the method 800 terminates after performing the operations at block 812. For example, the comparison of the benefit claim with the rules or requirements may cease responsive to determining that the claim is approved.

Returning to the description of block 810, if the benefit claim submitted by the provider does not meet the requirements or rules of the variant logic (e.g., the rules or requirements of the variant network), the benefit claim may proceed to be examined using the normal or non-variant logic. As a result, flow of the method 800 may proceed to decision point 814.

At decision point 814, the benefit claim is examined using non-variant, or normal, processing logic. For example, the benefit manager device 102 may examine the benefit claim relative to the requirements or criteria of other provider networks associated with the client. At decision point 816, a determination is made as to whether the benefit claim is allowed by a non-variant network. For example, the benefit manager device 102 can compare data representative of details of the claim to the requirements or criteria of one or more than one provider network associated with the client using the normal, or non-variant, processing logic. If the submitting provider is an approved provider within a provider network associated with the client and/or the other rules or criteria of the provider network are met by the submitted claim, then flow of the method 800 can proceed to block 818. However, if the submitted claim does not meet the requirements or criteria of one or more provider networks using the normal (e.g., non-variant) processing logic, then flow of the method 800 can proceed to block 820.

At block 818, the benefit claim is not denied. The benefit claim may be submitted for further processing to determine if other requirements for payment of the claim are met.

At block 820, the benefit claim may be denied. This denial can be communicated for the benefit manager device 102 to the provider submitting the claim.

In some embodiment, the systems and methods may determine whether providers in a provider network attached to a client have been suspended and/or whether providers in a network have one or more fee overrides. The provider data 406 and the override data 410 may include data structures that are queried or examined by the benefit manager device 102 in order to determine whether the provider is suspended and/or whether a fee override applies to a submitted claim.

FIG. 6 illustrates one example of a data structure 900 that is representative of the provider data 406 shown in FIG. 2 according to one example embodiment. While the data structure 900 is represented in FIG. 6 graphically, it should be appreciated that the data structure 900 may be implemented in a computer system (e.g., in a file allocation table and data associated therewith) in memory, drive storage, and/or cloud storage, or otherwise implemented.

The data structure 900 includes several records 902 each associated with a different provider. The records 902 each include several cells 904-916 that include data representative of which networks providers are included in, data representative of whether a provider has been suspended, and/or data representative of fee overrides corresponding to different providers. A provider may be suspended when the provider is disallowed (e.g., temporarily barred) from fulfilling prescriptions or prescription orders for one or more than one of the networks. This may occur when the provider has failed to obtain the necessary regulatory or legal certifications required by legislation or industry standards, when the provider is or employs one or more medical personnel subject to disciplinary action by a licensing board, when the provider has violated other requirements for participating in one or more networks, when the provider is suspended from providing medications pursuant to Medicare, or the like.

The cells 904 include data indicative of different providers. Each record 902 may have a different value in the corresponding cell 904 to indicate the provider for the record 902. In the illustrated embodiment, the providers are representatively named A, B, C, D, and E.

The cells 906-912 include data indicative of whether or not the provider and the corresponding record 902 is included in provider networks associated with different groups of the cells 906-912. For example, the cells 906 include data indicating that each of the providers in the cells 904 are included in the network having the identifier NG 154. The cells 908 include data indicating that providers A, B, and C are included in the provider network having the identifier 454, but the providers D and E are not included in this provider network. While values of one and zero are included in the cells 906-912 to indicate the inclusion or exclusion of corresponding providers in the various networks, optionally, other non-binary values or data may be used.

The cells 914 include data indicative of whether or not a corresponding provider has been suspended. The cells 914 have a value of one to indicate that a provider is suspended, have a different value (such as a value of zero) to indicate that the corresponding provider is not suspended. In some embodiments, other values may be used indicate suspension or non-suspension of the providers. For example, different values may be added to the cells 914 to indicate the cause or reason for the suspension of the provider, with different values indicating different causes or reasons for suspension. In the illustrated embodiment, only provider A is suspended, as indicated by the value of one in the cell 914 for the record 902 associated with provider A.

The cells 916 include data indicative of whether any fee overrides apply for the corresponding provider. The fee overrides may be indicated by identifiers representative of different override rules. An override rule can indicate the fee or financial amount that is to be charged for prescriptions or prescription orders submitted by that pharmaceutical provider, and in some embodiments, may include the basis, reason, or business rule for applying the fee override. In the illustrated example, a value of zero in the cells 916 may indicate that no fee override applies to the corresponding provider. In some embodiments, another value may be used. Other values may be used in the cells 916 to identify the fee overrides applicable to a provider, such as shown in the cell 916 for the provider B.

FIG. 7 illustrates one example of a data structure 1000 representative of the override data 410 shown in FIG. 2 according to one example embodiment. While the data structure 1000 is represented in FIG. 7 graphically, it should be appreciated that the data structure 900 may be implemented in a computer system (e.g., in a file allocation table and data associated therewith) in memory, drive storage, and/or cloud storage, or otherwise implemented.

The data structure 1000 includes several records 1002 each associated with a different fee override identifier. The fee override identifiers also may be included in the cells 916 of the data structure 900 to indicate which fee overrides or override rules apply to the corresponding providers.

The records 1002 in the data structure 1000 also include cells 1006 and 1008. The cells 1006 list an amount to be charged when the corresponding fee override applies to a benefit claim. For example, an amount of $25 may be charged for a medication associated with a pharmacy benefit claim subject to the override fee having the identifier 133.

The cells 1008 list the basis, reason, or business rule for applying the override rule. For example, the override rule associated with the identifier 133 has a basis of "Location." This basis can indicate that the override rule applies because of the geographic location or locations of the provider. For example, state legislation may mandate that providers within the state do not charge more than a designated amount for certain medications. In order to account for this restriction, the fee override rule may be used to process the claims and prevent more than the legislated amount from being charged for the medications.

The override rule associated with the basis of "K" can indicate that this override rule arises from a contractual agreement between the client and the pharmacy benefit manager. For example, some clients may wish to have reduced fees for one or more types of medications or pharmaceutical services relative to the fees otherwise charged for the same network of providers. This override rule can be provided for one or more than one of these providers to indicate that the fee override rule applies to reduce the fees charged for at least some of the medications provided by the providers. The override rule associated with the basis of "Other" can indicate that this override rule is due to one or more reasons other than the contractual basis or location basis.

Use of the data structures 900, 1000 can allow for the benefit manager device 102 to quickly determine which providers are suspended and/or which fee override rules to apply when processing a claim. Other approaches for determining provider suspension and/or determining which fee overrides to apply may involve significant changes to the software logic that processes claims. For example, instead of changing a designated setup of providers and fee overrides and/or instead of repeatedly changing the logic used in claim processing each time a provider is suspended or a fee override is implemented or changed, the data structures 900, 1000 allow for the suspension or override only to be changed across the entire system. This avoids the need to manipulate a large amount of data or change the claim processing logic across the entire system.

Additionally, instead of indicating the suspension of a provider within the data structure 900, other approaches may require changing the status of the provider in the numerous provider networks and contracts attached to those networks that include the provider. As another example, using fee overrides for one or more providers can require extensive changes to the provider networks that include the provider for which the override rule applies and/or for which are attached to the client. In contrast, the data structure 900 allows for the suspension of provider to be easily indicated and the data structures 900, 1000 allow for the override rules that are applicable to different providers to be easily modified.

In order to determine which fee override rule applies when multiple fee override rules are associated with a provider, the benefit manager device 102 can examine the data structure 1000. Different bases for fee overrides may be associated with different priorities. For example, the location basis for a fee override may be assigned a higher priority than a contractual basis for applying a fee override. This may result from the inability for the contract between the pharmacy benefit manager and the client to overcome location restrictions implemented by legislation. In contrast, the contract basis for a fee override may have a higher priority than other bases for the fee override. Responsive to determining that two or more fee override rules apply to a pharmaceutical provider, the benefit manager device 102 may select a fee override to apply based on the relative priorities of the fee overrides. The benefit manager device 102 can normally apply different rules based on characteristics of different claims, but these rules can be interrupted or circumvented when a fee override applies.

Figure 8:
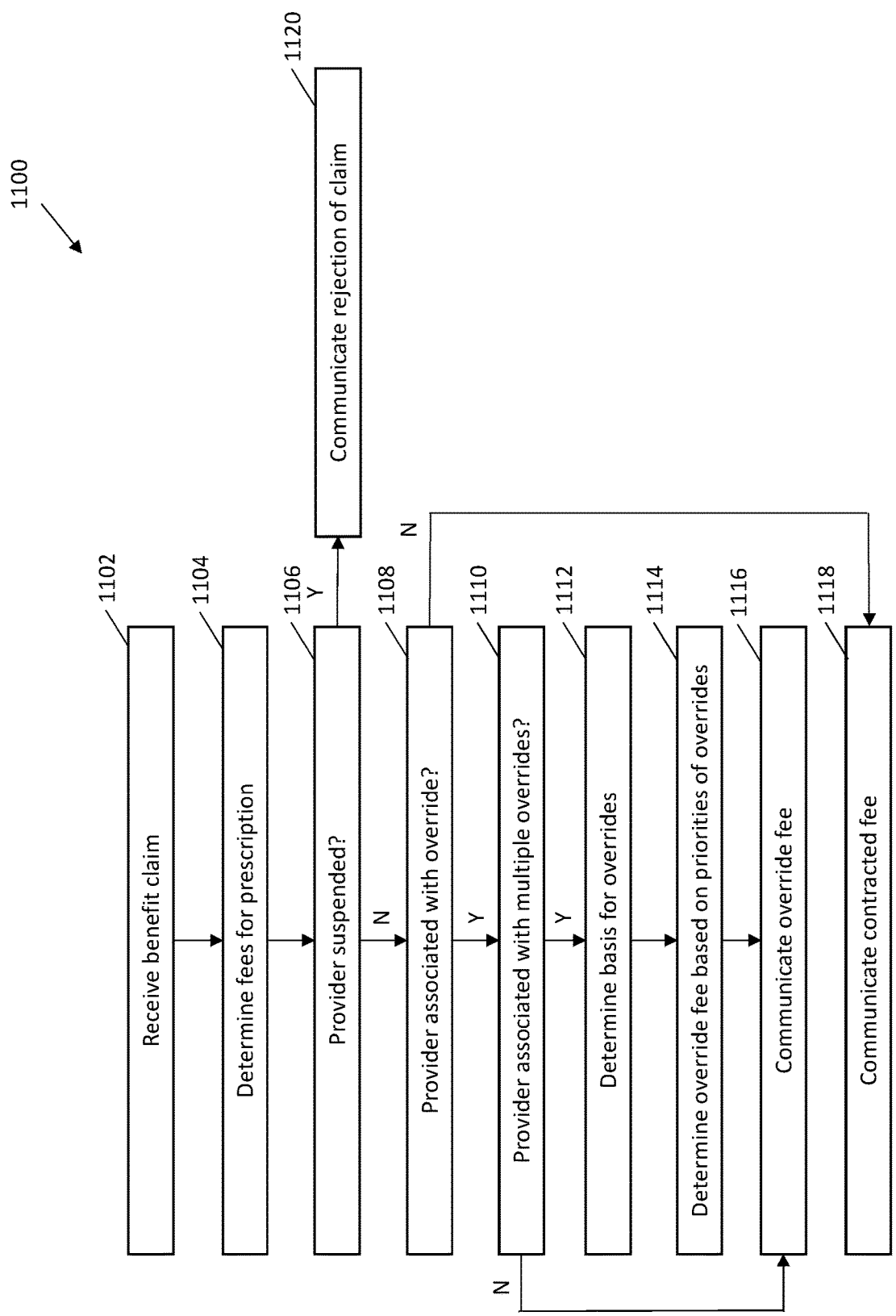
FIG. 8 is an example process flow illustrating a method for processing claims for pharmaceutical benefits according to an example embodiment.

FIG. 8 is an example process flow illustrating a method 1100 for processing claims for pharmaceutical benefits according to an example embodiment. At block 1102, a benefit claim is received. The benefit claim for pharmaceutical benefits may be received by a benefit manager device 102 from one or more than one pharmaceutical provider. This benefit claim can identify the member of insurance plan seeking the pharmaceutical benefit, the one or more than one medication for which the benefit is sought, the client providing the insurance plan, the pharmaceutical provider submitting the claim, and/or other information.

At block 1104, fees to be charged for fulfilling the prescription are determined. For example, assuming that the benefit claim is approved because the provider is an approved provider and other requirements for approving the claim within the provider network are met, the amount to be charged for fulfilling the pharmacy order may be determined. This may be determined using contractual agreement between the client and the pharmacy benefit manager. For example, the provider network in which the providers included may have agreed-upon amounts to be charged for various medications. These amounts may be part of the contractual agreement between the client and the pharmacy benefit manager. These amounts may be referred to as contracted fees.

At decision point 1106, a determination is made as to whether the provider has been suspended. This determination can be made by the benefit manager device 102 examining the provider data 406. For example, the benefit manager device 102 can examine the data structure 900 to determine whether a provider submitting the claim is suspended. If the provider submitting a claim is any of the providers B through E in the data structure 900, then the benefit manager device 102 may determine that the provider is not suspended. As a result, flow of the method 1100 can proceed toward decision point 1108.

However, if the claim is submitted by a provider indicated as being suspended by the cell 914 of the record 902 for the provider, the benefit manager device 102 can determine that the provider is suspended. As a result, flow of the method 1100 can proceed to block 1120.

At block 1120, the claim for pharmaceutical benefits is rejected and the rejection of this claim can be communicated to the provider. The benefit manager device 102 can determine that the suspension of the provider prevents the benefit claim from being approved, and can communicate this rejection and the basis for the rejection to the provider submitting the claim.

At decision block 1108, subsequent to determining that the provider is not suspended, a determination is made as to whether this provider is associated with one or more than one override fee. The benefit manager device 102 may determine whether the provider submitted a claim is submitted with one or more than one override fees by examining the cells 916 the data structure 900.

If the provider is associated with an override fee, then flow of the method 1100 may proceed to decision point 1110 in order to determine whether one or more additional override rules apply to this provider. However, if the provider is not associated with an override rule, then flow of the method 1100 may proceed to block 1116.

At decision point 1110, a determination is made as to whether the provider is associated with multiple override fees. In the example shown in the data structure 900, the provider C is associated with only a single override fee (having the identifier 133). The provider B, however, is associated with two override fees, identified as 213 and 133. If the provider is associated with multiple override fees, then flow of the method 1100 can proceed to block 1112 in order to determine which override fee to apply to the benefit claim. However, if the provider is associated with only a single override fee, then flow of the method may proceed to block 1116.

At block 1112, the bases for the multiple override fees associated with the provider are determined. For example, the benefit manager device 102 may examine the data structure 1000 to determine the basis for each of the multiple override fees applicable to the provider. In connection with the data structures 900, 1000, the benefit manager device 102 may determine that override fees 213 and 133 apply to the provider B. Examination of the data structure 1000 reveals that the override rule 213 has a contractual basis, while the override rule 133 has a location basis, as described above.

At block 1114, the override fee to be charged for the pharmaceutical claim is determined based on relative priorities of the override rules. As described above, different bases for overrides may be associated with different priorities. The location basis may be provided with a higher priority than a contractual basis, which is provided with a higher priority than other bases.

In connection with the provider B, the override fee 133 may have a higher priority than the override fee 213 due to the basis for the override fee 133 being "Location," which has a higher priority than the contractual basis for the fee 213. As a result, the benefit manager device 102 determines that the override fee of $25 of the fee 133 applies to the pharmacy benefit claim instead of the $35 fee associated with the contractual override fee 213.

At block 1116, the override fee that is determined from the one or more than one of the override rules applicable to the provider submitting the claim are communicated to the provider. The benefit manager device 102 may determine the override fee charged for the single override fee or the multiple override fees from the cells 1006 in the data structure 1000. Once the override fee is determined, this fee may be communicated to the pharmaceutical provider that submitted the claim.

At block 1118, the contracted fee is communicated to the pharmaceutical provider. In contrast to the override fee, the contracted fee may be the agreed-upon amount to charge for the one or more medications included in the claim for pharmacy benefits in a contractual agreement between the client and the pharmacy benefit manager. This contracted fee may be a base fee that is charged for all providers within a designated network, without any override fees or rules changing this amount. This fee may be communicated to the pharmaceutical provider after determining that no override fee applies (e.g., at block 1108).

Figure 9:
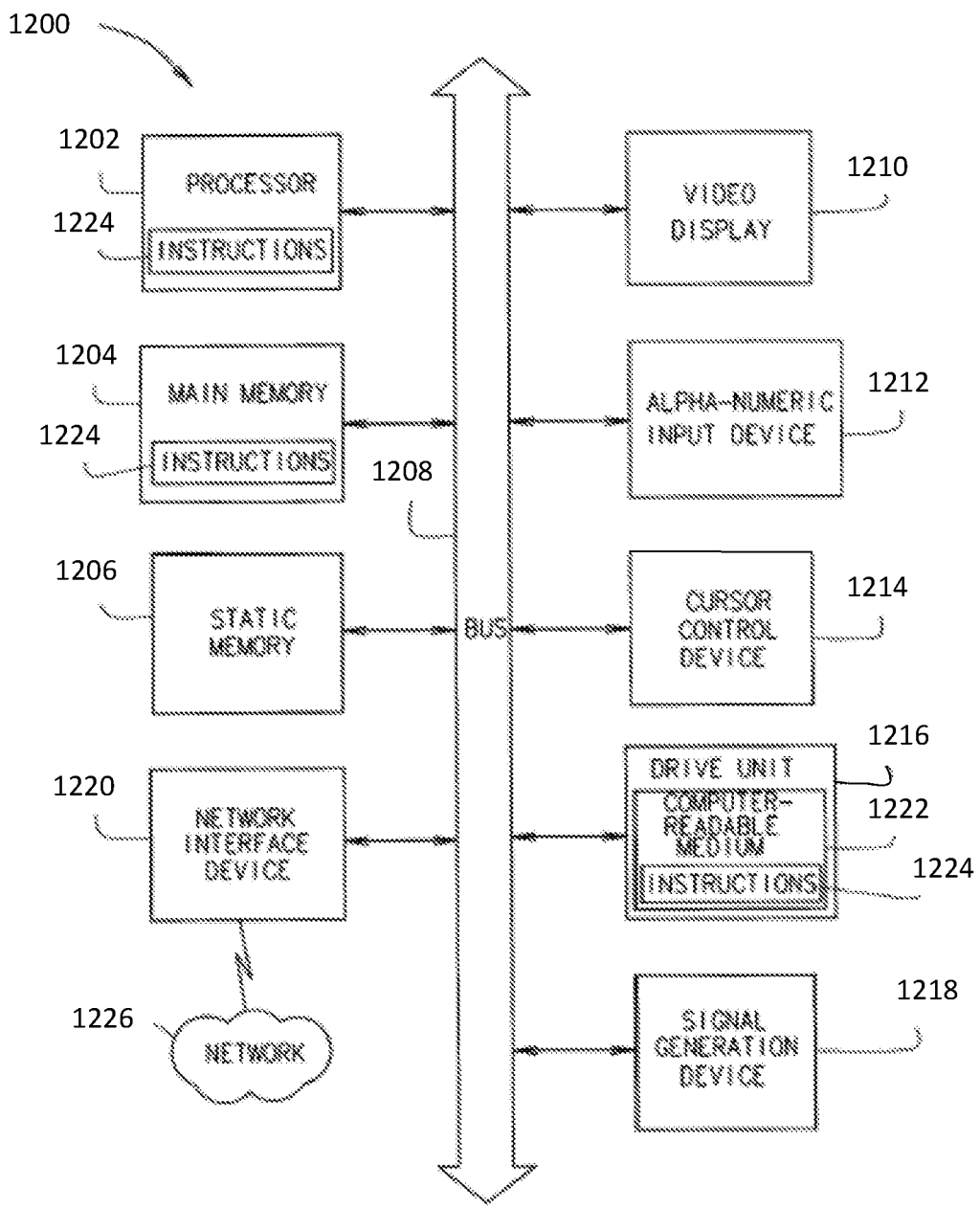
FIG. 9 shows a block diagram of a benefit manager device (shown in FIG. 1) in the example form of a computer system within which a set of instructions may be executed causing the machine to perform any one or more than one methods, processes, operations, or methodologies discussed herein.

FIG. 9 shows a block diagram of a pharmacy benefit manager device 102 (shown in FIG. 2) in the example form of a computer system 1200 within which a set of instructions may be executed causing the machine to perform any one or more than one methods, processes, operations, or methodologies discussed herein. The devices 102, 108, 206-230, for example, may include the functionality of the one or more than one computer systems 1200. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 1200 includes one or more processors 1202 (e.g., a central processing unit (CPU), a graphics processing unit (GPU) or both, etc.), a main memory 1204 and a static memory 1206, which communicate with each other via a bus 1208. The computer system 1200 further includes a video display unit 1210 (e.g., a liquid crystal display (LCD) or a cathode ray tube (CRT), etc.). The computer system 1200 also includes an alphanumeric input device 1212 (e.g., a keyboard, etc.), a cursor control device 1214 (e.g., a mouse, etc.), a drive unit 1216, a signal generation device 1218 (e.g., a speaker, etc.) and a network interface device 1220.

The drive unit 1216 includes a computer readable medium 1222 on which is stored one or more than one sets of instructions 1224 (e.g., software, etc.) embodying any one or more than one methodologies or functions described herein. The instructions 1224 may also reside, completely or at least partially, within the main memory 1204 and/or within the processor 1202 during execution thereof by the computer system 1200, the main memory 1204 and the processor 1202 also constituting non-transitory computer readable media. When loaded with the instructions 1224, the processor 1202 is a machine dedicated to only the present processes and methodologies.

The instructions 1224 may further be transmitted or received over a network 1226 via the network interface device 1220.

While the computer-readable medium 1222 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that is capable of storing or encoding a set of instructions for execution by the machine and that cause the machine to perform any one or more than one methodologies of the present invention. The term "Computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for a plurality of circuits or other electrical devices, which can be used in units, modules, systems, and subsystems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric devices may be configured to execute a computer-program that is embodied in a computer readable medium that is programmed to perform any number of the functions and features as disclosed. The computer readable medium may be non-transitory or in any form readable by a machine or electrical component.

The inventive subject matter may be represented in a variety of different embodiments of which there are many possible permutations.

In an example embodiment, a method includes determining whether a claim for a pharmaceutical benefit is to be processed using variant logic or non-variant logic, identifying one or more variant networks of pharmaceutical providers and determining whether details of the claim meet requirements of the one or more variant networks responsive to determining that the claim is to be processed using the variant logic, and, responsive to determining that the claim is to be processed using the non-variant logic, identifying one or more other networks of pharmaceutical providers and determining whether details of the claim meet requirements of the one or more other networks.

In another example embodiment, a system includes one or more processors configured to determine whether a claim for a pharmaceutical benefit is to be processed using variant logic or non-variant logic. The one or more processors are configured to identify one or more variant networks of pharmaceutical providers and determine whether details of the claim meet requirements of the one or more variant networks responsive to determining that the claim is to be processed using the variant logic. The one or more processors are configured to identify one or more other networks of pharmaceutical providers and determine whether details of the claim meet requirements of the one or more other networks responsive to determining that the claim is to be processed using the non-variant logic.

In another example embodiment, a method includes receiving a claim for a pharmaceutical benefit, examining data associated with a pharmaceutical provider submitting the claim for the pharmaceutical benefit to determine whether the pharmaceutical provider is suspended from dispensing a medication pursuant to the claim, and denying the claim for the pharmaceutical benefit responsive to the data indicating that the pharmaceutical provider is suspended. The data indicative of suspension of the pharmaceutical provider is stored in one or more storage devices along with an identifier of the pharmaceutical provider.

In an example embodiment, a system includes one or more processors of a pharmacy benefit manager device configured to receive a claim for a pharmaceutical benefit and to examine data associated with a pharmaceutical provider submitting the claim for the pharmaceutical benefit to determine whether the pharmaceutical provider is suspended from dispensing a medication pursuant to the claim. The one or more processors also are configured to deny the claim for the pharmaceutical benefit responsive to the data indicating that the pharmaceutical provider is suspended. The data indicative of suspension of the pharmaceutical provider is stored in one or more storage devices along with an identifier of the pharmaceutical provider.

Thus, methods and systems for logical data processing have been described. Although embodiments of the present invention have been described with reference to specific example embodiments, it will be evident that various modifications and changes may be made to these embodiments without departing from the broader spirit and scope of the embodiments of the invention.

Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A method comprising:
receiving a data processing request at a computing system, the data processing request identifying claims data to be compared to various sets of criteria according to a predefined sequence of the various sets of the criteria associated with analysis of a pharmacy benefit claim, wherein the predefined sequence of the various sets of the criteria is defined by a non-variant logic process;
determining whether the data processing request is to be processed according to the non-variant logic process or a variant logic process, wherein the variant logic process defines a modified, different sequence of the various sets of the criteria than the predefined sequence defined by the non-variant logic process, the data processing request is determined to be processed according to the variant logic process and not the non-variant logic process in responsive to the claims data indicating that: (a) a requested medication violates the criteria defined by the non-variant logic, (b) a requested amount of the requested medication violates the criteria defined by the non-variant logic, or (c) both the requested medication and the requested amount of the requested medication violates the criteria defined by the non-variant logic;
dynamically altering the predefined sequence of the various sets of the criteria in the non-variant logic process to the modified, different sequence of the sets of the criteria in the variant logic process in responsive to determining that the data processing request is to be processed using the variant logic process;
comparing the claims data identified by the data processing request with the sets of the criteria according to the modified, different sequence that is defined by the variant logic process; and processing the claims data according to the sets of the criteria according to the modified, different sequence that is defined by the variant logic process.

2. The method of claim 1, wherein processing the claims data according to the sets of the criteria in the modified, different sequence terminates and the pharmacy benefit claim is allowed responsive to the claims data meeting one or more of the sets of the criteria processed according to the variant logic process.

3. The method of claim 2, wherein processing the claims data according to the sets of the criteria in the modified, different sequence of the variant logic process terminates responsive to determining that the data meets the one or more of the sets of the criteria processed according to the variant logic process by ceasing to compare the claims data to the criteria of the sets of the criteria that are subsequent to the one or more sets processed according to the variant logic process in the modified, different sequence that is defined by the variant logic process.

4. The method of claim 1, wherein the data processing request identifies the requested medication to be administered by a pharmacy, and wherein the data processing request is determined to be processed according to the variant logic process responsive to the requested medication identified by the data processing request matching a pre-defined medication that is associated with the variant logic process.

5. The method of claim 1, wherein the data processing request identifies the requested amount of the requested medication to be administered by a pharmacy, and wherein the data processing request is determined to be processed according to the variant logic process responsive to the requested amount of the requested medication exceeding a pre-defined medication limit associated with the non-variant logic process.

6. The method of claim 1, wherein processing the claims data according to the sets of the criteria in the modified, different sequence that is defined by the variant logic process results in the data meeting the criteria in at least one of the sets of criteria, and wherein processing the data according to the sets of the criteria in the predefined sequence that is defined by the non-variant logic process results in the claims data not meeting the criteria in at least one of the sets of criteria.

7. The method of claim 1, wherein the sets of the criteria define requirements of various pharmaceutical networks.

8. A tangible and non-transitory computer-readable storage medium comprising instructions that direct at least one processor to:
receive a data processing request at a computing system, the data processing request identifying claims data to be compared to various sets of criteria according to a predefined sequence of the various sets of the criteria associated with analysis of a pharmacy benefit claim, wherein the predefined sequence of the various sets of the criteria is defined by a non-variant logic process;
determine whether the data processing request 1s to be processed according to the non-variant logic process or a variant logic process, wherein the variant logic process defines a modified, different sequence of the various sets of the criteria than the predefined sequence defined by the non-variant logic process, the data processing request is determined to be processed according to the variant logic process and not the non-variant logic process responsive to the claims data indicating that (a) a requested medication violates the criteria defined by the non-variant logic, (b) a requested amount of the requested medication violates the criteria defined by the non-variant logic, or (c) that both the requested medication and the requested amount of the requested medication violates the criteria defined by the non-variant logic;
dynamically alter the predefined sequence of the various sets of the criteria in the non-variant logic process to the modified, different sequence of the sets of the criteria in the variant logic process responsive to determining that the data processing request is to be processed using the variant logic process;
compare the claims data identified by the data processing request with the sets of the criteria in the modified, different sequence that is defined by the variant logic process; and
process the claims data according to the sets of the criteria in the modified, different sequence that is defined by the variant logic process.

9. The computer-readable storage medium of claim 8, wherein the instructions direct the at least one processor to process the claims data according to the sets of the criteria in the modified, different sequence terminates and the pharmacy benefit claim is allowed responsive to the claims data meeting one or more of the sets of the criteria processed according to the variant logic process.

10. The computer-readable storage medium of claim 9, wherein the instructions direct the at least one processor to process the claims data according to the sets of the criteria in the modified, different sequence of the variant logic process terminates responsive to determining that the data meets the one or more of the sets of the criteria processed according to the variant logic process by ceasing to compare the claims data to the criteria of the sets of the criteria that are subsequent to the one or more sets processed according to the variant logic process in the modified, different sequence that is defined by the variant logic process.

11. The computer-readable storage medium of claim 8, wherein the data processing request identifies the requested medication to be administered by a pharmacy, and wherein the instructions direct the at least one processor to process the data processing request according to the variant logic process responsive to the requested medication identified by the data processing request matching a pre-defined medication that is associated with the variant logic process.

12. The computer-readable storage medium of claim 8, wherein the data processing request identifies the requested amount of the requested to be administered by a pharmacy, and wherein the instructions direct the at least one processor to process the data processing request according to the variant logic process responsive to the requested amount of the requested medication identified by the data processing request exceeding a pre-defined medication limit associated with the non-variant logic process.

13. The computer-readable storage medium of claim 8, wherein the sets of the criteria define requirements of various pharmaceutical networks.

* * * * *